United States Patent [19]

Finlayson

[11] 4,208,218

[45] Jun. 17, 1980

[54] VISCOSITY INCREASING ADDITIVE FOR NON-AQUEOUS FLUID SYSTEMS

[75] Inventor: Claude M. Finlayson, Houston, Tex.

[73] Assignee: NL Industries, Inc., New York, N.Y.

[21] Appl. No.: 890,809

[22] Filed: Mar. 27, 1978

[51] Int. Cl.$^2$ .......................... B01J 13/00; C09K 3/00
[52] U.S. Cl. ............................ 106/287.25; 260/448 C; 252/316; 106/287.3
[58] Field of Search ............ 106/308 N, 308 F, 287.3; 260/448 C; 252/316

[56] References Cited

U.S. PATENT DOCUMENTS

| | | | |
|---|---|---|---|
| 2,531,427 | 11/1950 | Hauser | 252/316 |
| 3,422,185 | 1/1969 | Kuritzkes | 424/61 |
| 3,537,994 | 11/1970 | House | 252/13 |
| 3,864,294 | 2/1975 | Busch, Jr. | 106/308 N |
| 3,977,894 | 8/1976 | White et al. | 106/288 Q |
| 4,053,493 | 10/1977 | Oswald | 260/448 C |
| 4,081,496 | 3/1978 | Finlayson | 260/864 |
| 4,105,578 | 8/1978 | Finlayson et al. | 252/316 |

OTHER PUBLICATIONS

Organophilic Bentonites, J. W. Jordan, pp. 294–306, Journal of Physical Chem. & Colloid, 53, 1949.

*Primary Examiner*—Theodore Morris
*Attorney, Agent, or Firm*—Gary M. Nath

[57] ABSTRACT

An organoclay rheological additive for non-aqueous fluid systems comprising an organophilic clay gellant comprising the reaction product of a smectite-type clay having a cation exchange capacity of at least 75 milliequivalents per 100 grams of clay and a methyl benzyl dialkyl ammonium compound or a dibenzyl dialkyl ammonium compound wherein the alkyl groups contain specific amounts of 8 to 22 carbon atoms and the amount of said ammonium compound reacted with said clay being from 100 to 130 milliequivalents per 100 grams of clay based upon 100% active clay.

6 Claims, No Drawings

VISCOSITY INCREASING ADDITIVE FOR NON-AQUEOUS FLUID SYSTEMS

In the prior art many different types of rheological agents are used in non-aqueous fluid systems such as paints, varnishes, enamels, waxes, epoxies, mastics and the like. These fluid systems often contain finely divided suspended materials, such as pigments and the like, and the rheological agent is added to thicken the system to produce a thixotropic flow behavior with high viscosity at a low shear rate.

Various organo modified clays and other inorganic and organic compounds have been used in the past to produce these rheological effects. The organophilic clays, however, which have been used by the prior art require the use of polar solvent activators which must be added to the system to produce the rheological effect. If the polar solvent activators are not used, the desired rheological properties, viscosity build, pigment setting control, and sag control are not fully achieved, that is, only a portion of the clay's thickening ability is obtained. In addition, when the polar solvent activators are eliminated, the compositions containing organo-clays known to date will increase in viscosity on storage, thus having a deleterious effect on the original rheological properties designed into the system.

Some of these polar additives, such as acetone, alcohols and the like have low flash points and therefore should be avoided if possible. In addition, these polar additives must be added as a separate step at the time of preparing the systems. This separate step adds to the cost of the system. In addition, some polar additives may react with other system formulation components and eliminate essential rheological properties.

In contrast to the prior art, a self-activating rheological agent has been produced by the instant invention which does not require the addition of polar solvent activators.

A self-activating rheological agent has been produced comprising the reaction product of a methyl benzyl dialkyl ammonium compound or a dibenzyl dialkyl ammonium compound wherein the alkyl group is selected from the group consisting of 14 to 22 carbon atoms wherein 20 to 35% have 16 carbon atoms and 60 to 75% having 18 carbon atoms, and 8 to 20 carbon atoms wherein at least 5% have 8 to 14 carbon atoms, and a smectite-type clay having a cation exchange capacity of at least 75 milliequivalents per 100 grams of said clay, and wherein the amount of said ammonium compound is from 100 to 130 milliequivalents per 100 grams of said clay, 100% active clay basis.

The clays used to prepare the oganophilic clay gellants of this invention are smectite-type clays which have a cation exchange capacity of at least 75 milliequivalents per 100 grams of clay. Particularly desirable types of clay are the naturally-occurring Wyoming varieties of swelling bentonites and like clays, and hectorite, a swelling magnesium-lithium silicate clay.

The clays, especially the bentonite type clays, are preferably converted to the sodium form if they are not already in this form. This can conveniently be done by preparing an aqueous clay slurry and passing the slurry through a bed of cation exchange resin in the sodium form. Alternatively, the clay can be mixed with water and a soluble sodium compound such as sodium carbonate, sodium hydroxide and the like, and shearing the mixture with a pugmill or extruder.

Smectite-type clays prepared synthetically by either a pneumatolytic or, preferably a hydrothermal synthesis process can also be used to prepare the present organophilic clays. Representative of such clays are montmorillonite, bentonite, beidellite, hectorite, saponite, and stevensite. These clays may be synthesized hydrothermally by forming an aqueous reaction mixture in the form of a slurry containing mixed hydrous oxides or hydroxides of the desired metals with or without, as the case may be, sodium (or alternate exchangeable cation of mixture thereof) fluoride in the proportions for the particular synthetic smectite desired. The slurry is then placed in an autoclave and heated under autogenous pressure to a temperature within the range of approximately 100° to 325° C., preferably 274° to 300° C., for a sufficient period of time to form the desired product.

The cation exchange capacity of the smectite-type clays can be determined by the well-known ammonium acetate method.

The quaternary ammonium compounds which are reacted with these smectite-type clays is a methyl benzyl or dibenzyl dialkyl ammonium salt wherein the alkyl groups comprise from 14 to 22 carbon atoms, preferably 16 or 18 carbon atoms and most preferably 20% to 35% of the alkyl radicals contain 16 carbon atoms and 60% to 75% contain 18 carbon atoms or 8 to 20 carbon atoms wherein at least 5% have 8 to 14 carbon atoms and preferably at least 20% have 12 carbon atoms. The salt anion is preferably selected from the group consisting of chloride and bromide, and mixtures thereof, and is more preferably chloride, although other anions such as acetate, hydroxide, nitrite, etc., may be present in the quaternary ammonium salt to neutralize the quaternary ammonium cation. These quaternary ammonium salts can be represented by the formula:

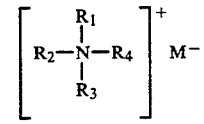

wherein $R_1$ is $CH_3$ or $C_6H_5CH_2$; $R_2$ is $C_6H_5CH_2$; and $R_3$ and $R_4$ are alkyl groups containing long chain alkyl radicals having either 14 to 22 carbon atoms, preferably 16 or 18 carbon atoms, and most preferably wherein 20% to 35% of said long chain alkyl radicals contain 16 carbon atoms and 60% to 75% of said long chain alkyl radicals contain 18 carbon atoms, or 8 to 20 carbon atoms wherein at least 5% have 8 to 14 carbon atoms and most preferably at least 20% 12 carbon atoms, and wherein M is selected from the group consisting of chloride, bromide, nitrite, hydroxyl, acetate, methyl, sulfate, and mixtures thereof.

The preferred quaternary ammonium salts are methyl benzyl dihydrogenated tallow ammonium chloride and methyl benzyl dicoconut fatty acid ammonium chloride. Commercially prepared hydrogenated tallow typically analyzes 2.0% $C_{14}$, 0.5% $C_{15}$, 29.0% $C_{16}$, 1.5% $C_{17}$; 66.0% $C_{18}$ and 1.0% $C_{20}$ alkyl groups. Commercially prepared coconut fatty acid typically analyses 5–9% $C_8$, 4–10% $C_{10}$, 44–51% $C_{12}$, 13–18% $C_{14}$, 7–10% $C_{16}$, and 1–4% $C_{18}$ alkyl groups.

The organophilic clays of this invention can be prepared by admixing the clay, quaternary ammonium compound and water together, preferably at a temperature within the range of from 100° F. (38° C.) to 180° F.

(82° C.), more preferably from 140° F. (60° C.) to 170° F. (77° C.) for a period of time sufficient for the organic quaternary ammonium compound to react with the clay particles, followed by filtering, washing, drying, and grinding. If using the organophilic clays in emulsions, the drying and grinding steps may be eliminated. When admixing the clay, quaternary ammonium compound and water in such concentrations that a slurry is not formed, then the filtration and washing steps can be eliminated.

Preferably, the clay is dispersed in water at a concentration from about 1% to 7% by weight, the slurry optionally centrifuged to remove non-clay impurities which constitute about 10% to about 50% by weight of the starting clay composition; the slurry agitated and heated to a temperature in the range of from 140° F. (60° C.) to 170° F. (77° C.); the quaternary amine salt added in the desired milliequivalent ratio, preferably as a liquid in isopropanol or dispersed in water; and the agitation continued to effect the reaction.

The amount of the quaternary ammonium compound added to the clay for purposes of this invention must be sufficient to impart to the clay the enhanced dispersion characteristics desired. The milliequivalent ratio is defined as the number of milliequivalents of the quaternary ammonium compound in the organophilic clay, per 100 grams of clay, 100% active basis. The organophilic clays of this invention have a milliequivalent ratio of from 100 to 130. At lower milliequivalent ratios the organophilic clays are ineffective gellants even though they may be effective gellants when dispersed in a conventional manner with a polar additive. At higher milliequivalent ratios, the organophilic clays are poor gellants. However, the preferred milliequivalent ratio within the range of from 100 to 130 will vary depending on the characteristics of the organic system to be gelled by the organophilic clay.

The non-aqueous fluid compositions in which the self activating organophilic clays are useful include paints, varnishes, enamels, waxes, epoxies, mastics, adhesives, cosmetics and the like. These fluids may be prepared by any conventional method, such as with colloid mills, roller mills, ball mills, and high speed dispersers, in which the fluid pigment materials become well dispersed in the organic vehicle by the high shear used in processing.

The organophilic clay gellant is employed in amounts sufficient to obtain the desired rheological properties such as high viscosity at low shear rates, control of sagging of fluid films and prevention of settling and hard packing of pigments present in the fluid compositions. Amounts of the organophilic clay gellant employed in the non-aqueous fluid system should preferably be between about 0.1% and about 5.0% based on the weight of the treated non-aqueous fluid system and preferably between 0.3% and 2.0% to yield the desired rheological effects.

The following examples are given to illustrate the invention, but are not deemed to be limiting thereof. All percentages given throughout the specification are based upon weight unless otherwise indicated.

EXAMPLE 1

About 1500 grams of a 29 slurry of Wyoming bentonite in water which had been previously treated by centrifugation to remove all non-clay impurities and ion-exchanged to provide the clay in the sodium form was heated to about 150° F. and combined with 39.3 grams of 77.8% active methyl benzyl dihydrogenated tallow ammonium chloride. The mixture was stirred for 45 minutes, filtered to remove solids, dried at 150° F. and finally ground to yield an organophilic clay gellant containing 112.0 milliequivalents of quaternary ammonium compound per 100 grams of clay.

The methyl benzyl dihydrogenated tallow ammonium bentonite was employed as the rheological additive in a gloss enamel, using a mixture of 95% methanol and 5% water as the polar solvent activator, in one case, and eliminating the polar activator in the other.

For comparison, two enamels were made using dimethyl dihydrogenated tallow ammonium bentonite as the organophilic clay. In one case the mixture of 95% methanol and 5% water was used as the polar solvent activator and no polar solvent activator used in the other. In addition, an enamel was prepared without the addition of any rheological additive.

The enamels were prepared using a high speed disperser using the following formulation:

TABLE I

| Organoclay: | methyl benzyl dihydrogenated tallow ammonium bentonite | | dimethyl dihydrogenated tallow ammonium bentonite | | No Organophilic clay |
|---|---|---|---|---|---|
| | With Activator | Without Activator Pounds | With Activator | Without Activator | |
| Long oil soya alkyd resin solution | 72.8 | 72.8 | 72.8 | 72.8 | 72.8 |
| Mineral Spirits, Rule 66 type | 86.5 | 86.5 | 86.5 | 86.5 | 86.5 |
| Methyl benzyl dihydrogenated tallow ammonium bentonite | 9.8 | 9.8 | — | — | — |
| Dimethyl dihydrogenated tallow ammonium bentonite | — | — | 9.8 | 9.8 | — |
| 95% Methanol - 5% water mixture | 3.2 | — | 3.2 | — | — |
| Titanium dioxide, enamel grade | 325.0 | 325.0 | 325.0 | 325.0 | 325.0 |
| Grind and then add: | | | | | |
| Long oil soya alkyd resin solution | 410.2 | 410.2 | 410.2 | 410.2 | 410.2 |
| Mineral spirits, Rule 66 type | 107.5 | 107.5 | 107.5 | 107.5 | 107.5 |
| 24% Lead Naphthenate | 7.1 | 7.1 | 7.1 | 7.1 | 7.1 |
| 4% Calcium Naphthenate | 8.0 | 8.0 | 8.0 | 8.0 | 8.0 |
| 6% Cobalt Naphthenate | 2.9 | 2.9 | 2.9 | 2.9 | 2.9 |

TABLE I-continued

| Organoclay: | methyl benzyl dihydrogenated tallow ammonium bentonite | | dimethyl dihydrogenated tallow ammonium bentonite | | No Organophilic clay |
|---|---|---|---|---|---|
|  | With Activator | Without Activator Pounds | With Activator | Without Activator |  |
| Antiskinning Agent | 1.0 | 1.0 | 1.0 | 1.0 | 1.0 |
|  | 1034.0 | 1030.8 | 1034.0 | 1030.8 | 1021.0 |

Viscosity data for these enamel compositions are given in Table II. The viscosity determinations were made using a Brookfield RVT cone and plate viscometer at 10 rpm, equivalent to a shear rate of 40 sec.$^{-1}$.

TABLE II

| Organophilic Clay | Brookfield viscosities (cps) at 40 sec.$^{-1}$ | |
|---|---|---|
|  | With activator | Without activator |
| Methyl Benzyl dihydrogenated tallow ammonium bentonite | 307 | 300 |
| Dimethyl dihydrogenated tallow ammonium bentonite | 341 | 186 |
| No organophilic clay | — | 150 |

The table shows that when conventionally employed dimethyl dihydrogenated tallow ammonium bentonite is employed in the enamel without the use of a polar solvent activator, only a small increase in viscosity is seen over that of the enamel containing no organophilic clay rheological additive. When the methanol and water mixture is added, activation of the organoclay occurs and significant viscosity increase is obtained.

In contrast when the methyl benzyl dihydrogenated tallow ammonium bentonite is used, the viscosity obtained does not depend upon whether a polar solvent activator is used; full rheological properties (including viscosity, sag control and pigment suspension) are achieved in both cases.

EXAMPLE 2

About 1500 grams of a 2.8% slurry of Wyoming bentonite in water which had been previously treated by centrifugation to remove all non-clay impurities and ion-exchanged to provide the clay in the sodium form was heated to about 150° F. and combined with 28.0 grams of 90.0% active methyl benzyl dicoconut fatty acid ammonium chloride. The mixture was stirred for 45 minutes, filtered to remove solids, dried at 150° F. and finally ground to yield an organophilic clay gellant containing 122.7 milliequivalents of quaternary ammonium compound per 100 grams of clay.

The methyl benzyl dicoconut fatty acid ammonium bentonite was employed as the rheological additive in the gloss enamel formulation of Example 1, in one case incorporating a 95% methanol and 5% water mixture as the polar solvent activator, and eliminating the activator in the other.

The results indicate that the viscosity build, thixotropy, sag control and pigment settling control properties were essentially equivalent in both the presence and absence of a polar solvent activator. This would not occur with conventionally employed organophilic clays.

EXAMPLE 3

The procedure of Example 1 was repeated except that a different non-aqueous system, namely a basic lead silicochromate-alkyl primer was employed as set forth below instead of the gloss enamel.

The following formulation was prepared on a high speed disperser:

|  | Pounds With Activator | Pounds Without Activator |
|---|---|---|
| Medium Oil Linseed and Soya Alkyd Resin Solution | 505 | 505 |
| Mineral Spirits | 101 | 101 |
| Basic Lead Silico Chromate | 519 | 519 |
| Iron Oxide | 43 | 43 |
| Zinc Oxide (Acicular) | 43 | 43 |
| Methyl Benzyl Dihydrogenated Tallow Ammonium Bentonite | 5 | 5 |
| Methanol - Water (95-5) | 1.7 | — |
| Grind Add: |  |  |
| Lead Naphthenate (24%) | 10.5 | 10.5 |
| Cobalt Naphthenate (6%) | 4.2 | 4.2 |
| Manganese Naphthenate (6%) | 4.2 | 4.2 |
| Anti-Skinning Agent | 3.7 | 3.7 |
| TOTAL | 1240.3 | 1238.6 |

The results indicate that viscosity build, thixotropy, sag control and pigment settling control properties were essentially equivalent in both the presence and absence of a polar solvent activator. This would not occur with conventionally employed organophilic clays.

EXAMPLE 4

The procedure of Example 1 was repeated except that the alkyd-urea baking enamel non-aqueous system described below was employed instead of the gloss enamel.

The formulation was prepared on a high speed disperser:

|  | Pounds With Activator | Pounds Without Activator |
|---|---|---|
| Short Oil Castor Alkyd Resin Solution (50% N.V.) | 493 | 493 |
| Urea-Formaldehyde Resin (60% N.V.) | 98 | 98 |
| Xylol | 121 | 121 |
| Titanium Dioxide (Rutile) | 240 | 240 |
| Methyl Benzyl Dihydrogenated Tallow Ammonium Hectorite | 4.5 | 4.5 |
| Methanol-Water (95-5) | 1.4 | — |
| Butanol | 28 | 28 |
| Grind Add: |  |  |
| Cobalt Naphthenate (6%) | 0.4 | 0.4 |
| Manganese Naphthenate (6%) | 0.4 | 0.4 |
| TOTAL | 986.7 | 985.3 |

The results indicate that viscosity build, thixotropy, sag control and pigment settling control properties were essentially equivalent in both the presence and absence of a polar solvent activator. This would not occur with conventionally employed organophilic clays.

EXAMPLE 5

The procedure of Example 1 was repeated except that the exterior wood stain non-aqueous system described below was employed instead of the gloss enamel, and that a ball mill was used rather than a high speed disperser.

|  | With Activator Pounds | Without Activator Pounds |
|---|---|---|
| Charge to a ball mill: |  |  |
| Long oil soya alkyd resin solution (70% N.V.) | 345 | 345 |
| Aromatic Mineral Spirits | 104 | 104 |
| Mineral Spirits | 276 | 276 |
| Chromium Oxide | 45 | 45 |
| Methyl benzyl dihydrogenated tallow ammonium bentonite | 6 | 6 |
| Methanol-Water (95-5) | 2 | — |
| Grind Add: |  |  |
| Pentachlorophenol Solution (5%) | 5.2 | 5.2 |
| Lead Naphthenate (24%) | 5.2 | 5.2 |
| Cobalt Napthenate (6%) | 1.8 | 1.8 |
| Total | 790.2 | 788.2 |

The results indicate that pigment suspension was essentially equivalent in both the presence and absence of a polar solvent activator. This would not occur with conventionally employed organophilic clays.

EXAMPLE 6

The procedure of Example 1 was repeated except that a solvent based caulking compound (as described below) was employed instead of the glass enamel of Example 1. The caulk was prepared using a Sigma Mixer.

| CAULKING COMPOUND |  |  |
|---|---|---|
|  | With Activator Pounds | Without Activator Pounds |
| Calcium Carbonate | 800 | 800 |
| Fibrous Talc | 200 | 200 |
| Blown Soya Oil | 246 | 246 |
| Polybutene Resin | 112 | 112 |
| Soya Fatty Acids | 16 | 16 |
| Mineral Spirits | 60 | 60 |
| Cobalt Naphthenate (6%) | 4 | 4 |
| Methyl benzyl dihydrogenated tallow ammonium bentonite | 7 | 7 |
| Methanol-Water (95-5) | 2.2 | — |
| Total | 1447.2 | 1445.0 |

The results indicate that sag and slump control properties were essentially equivalent in both the presence and absence of a polar solvent activator. This would not occur with conventionally employed organophilic clays.

EXAMPLE 7

The procedure of Example 1 was repeated except that a different non-aqueous system (as described below) was employed instead of the gloss enamel of Example 1.

The following formulation was prepared using a Lighting mixer:

| Hair Cream | Pounds With Activator | Pounds Without Activator |
|---|---|---|
| U.S.P. Mineral Oil | 35.0 | 35.0 |
| Ethoxylated Hydrogenated Castor Oil | 8.0 | 8.0 |
| Petrolatum | 53.0 | 53.0 |
| Methyl Benzyl Dihydrogenated Tallow Ammonium Bentonite | 3.0 | 3.0 |
| Propylene Carbonate | 1.0 | — |
| TOTAL | 100.0 | 99.0 |

The results indicate that the viscosity build was essentially equivalent in both the presence and absence of polar solvent activator. This would not occur with conventionally employed organophilic clays.

EXAMPLE 8

The procedure of Example 1 was repeated except that a different non-aqueous system (as described below) was employed instead of the gloss enamel of Example 1.

The following formulation was prepared using a Lightning mixer and packaged in aerosol cans:

| Aerosol Antiperspirant | Pounds With Activator | Pounds Without Activator |
|---|---|---|
| Isopropyl Myristate | 4.0 | 4.0 |
| Silicon Oil (Polysiloxane) | 6.0 | 6.0 |
| Methyl Benzyl Dihydrogenated Tallow Ammonium Bentonite | 3.0 | 3.0 |
| Propylene Carbonate | 1.0 | — |
| Mix Add: |  |  |
| Aluminum Chlorohydrate | 5.0 | 5.0 |
| Mix and Package With Propellant (Isobutane) | 81.0 | 81.0 |
| TOTAL | 100.0 | 99.0 |

The results indicate that the viscosity build and the aluminum chlorohydrate suspension in the aerosol package where essentially equivalent in both the presence and absence of polar solvent activator. This would not occur with conventionally employed organophilic clays.

EXAMPLE 9

The procedure of Example 1 was repeated except that a different non-aqueous system (as described below) was employed instead of the gloss enamel of Example 1.

| One-Package-Epoxy-Adhesive (Prepared on a 3-roll mill) | Pounds With Activator | Pounds Without Activator |
|---|---|---|
| Epoxy Resin | 815 | 815 |
| Dicyandiamide | 45 | 45 |
| Aluminum Oxide | 180 | 180 |
| Methyl Benzyl Dihydrogenated Tallow Ammonium Hectorite | 15 | 15 |
| Methanol-Water (95-5) | 5 | — |
| TOTAL | 1060 | 1055 |

The results indicate that viscosity build, thixotropy, and sag control properties were essentially equivalent in both the presence and absence of a polar solvent activator. This would not occur with conventionally employed organophilic clays.

What is claimed is:

1. A self-activating organophilic clay rheological composition useful as an additive for non-aqueous fluid systems which is capable of increasing the viscosity of said non-aqueous fluid systems without the addition of a polar organic dispersant, which comprises the reaction product of a material selected from the group consisting of a dibenzyl dialkyl ammonium compound wherein the alkyl group contains 14 to 22 carbon atoms and wherein 20 to 35% have 16 carbon atoms and 60 to 75% having 18 carbon atoms, and a methyl benzyl dialkyl ammonium compound or a dibenzyl dialkyl ammonium compound wherein the alkyl group contains 8 to 20 carbon atoms wherein at least 5% have 8 to 14 carbon atoms, and a smectite-type clay having a cation exchange capacity of at least 75 milliequivalents per 100 grams of said clay, and wherein the amount of said ammonium compound is from 100 to 130 milliequivalents per 100 grams of said clay, 100% active clay basis.

2. The composition of claim 1 wherein the dibenzyl dialkyl ammonium compound is dibenzyl dihydrogenated tallow ammonium chloride.

3. The composition of claim 1 wherein the methyl benzyl dialkyl ammonium compound is methyl benzyl dicoconut fatty acid ammonium chloride.

4. The composition of claim 1 wherein the dibenzyl dialkyl ammonium compound is dibenzyl dicoconut fatty acid ammonium chloride.

5. The non-aqueous fluid system of claim 1 wherein said organophilic clay composition comprises from 0.1% to 5% by weight of said non-aqueous fluid system.

6. The non-aqueous fluid system of claim 1 wherein said organophilic clay composition comprises from 0.3% to 2.0% by weight of said non-aqueous fluid system.

* * * * *